US008888779B2

(12) United States Patent
Senn et al.

(10) Patent No.: US 8,888,779 B2
(45) Date of Patent: Nov. 18, 2014

(54) LOCKING SCREW FOR AN INTRAMEDULLARY NAIL

(75) Inventors: Peter Senn, Waldenburg (CH); André Schlienger, Arlesheim (CH); Markus Buettler, Mümliswil (CH)

(73) Assignee: DePuy Synthes Products, LLC, Raynham, MA (US)

( * ) Notice: Subject to any disclaimer, the term of this patent is extended or adjusted under 35 U.S.C. 154(b) by 2398 days.

(21) Appl. No.: 11/221,648

(22) Filed: Sep. 7, 2005

(65) Prior Publication Data
US 2006/0064095 A1 Mar. 23, 2006

Related U.S. Application Data (63) Continuation of application No. PCT/CH03/00157, filed on Mar. 7, 2003.

(51) Int. Cl.
*A61B 17/72* (2006.01)
*A61B 17/86* (2006.01)

(52) U.S. Cl.
CPC ....... *A61B 17/725* (2013.01); *A61B 2017/8655* (2013.01)
USPC .......................................................... 606/66

(58) Field of Classification Search
USPC ............. 606/62–68, 286, 293, 313, 328, 314, 606/319; 411/214–219, 446, 447, 452, 528, 411/529
See application file for complete search history.

(56) References Cited

U.S. PATENT DOCUMENTS

| 969,382 | A | * | 9/1910 | Mack ............................ 411/446 |
| 2,834,342 | A | | 5/1958 | Yost |
| 3,255,747 | A | | 6/1966 | Cochran et al. |
| 3,374,786 | A | * | 3/1968 | Callender, Jr. .................. 606/65 |
| 3,433,220 | A | | 3/1969 | Zickel |
| 3,650,309 | A | * | 3/1972 | Neuschotz ..................... 411/110 |
| 4,095,591 | A | | 6/1978 | Graham, Jr. et al. |

(Continued)

FOREIGN PATENT DOCUMENTS

| CH | 668 173 | 12/1988 |
| CH | 674 613 | 6/1990 |

(Continued)

OTHER PUBLICATIONS

International Search Report for International Application No. PCT/CH03/00157, mailed Oct. 20, 2003, German language version.

(Continued)

*Primary Examiner* — Eduardo C Robert
*Assistant Examiner* — Steven Cotroneo
(74) *Attorney, Agent, or Firm* — Fay Kaplun & Marcin, LLP (57) ABSTRACT

A locking screw for an intramedullary nail having at least one transverse hole. The locking screw has a central longitudinal axis and includes a screw shank, which is at least partially provided with an external thread, and a screw head. The diameter of the screw head is greater than the outer diameter of the external thread, and the screw head includes a passage extending generally parallel to the longitudinal axis of the screw and the external thread. The passage is configured to receive a longitudinal wedge element. As a result, any gap between the locking screw and the intramedullary nail is eliminated and the screw is wedged in position in the transverse hole of the intramedullary nail.

20 Claims, 7 Drawing Sheets

(56) References Cited

U.S. PATENT DOCUMENTS

| | | | |
|---|---|---|---|
| 4,103,683 A | 8/1978 | Neufeld | |
| 4,172,452 A | 10/1979 | Forte et al. | |
| 4,274,163 A | 6/1981 | Malcom et al. | |
| 4,438,762 A | 3/1984 | Kyle | |
| 4,494,535 A | 1/1985 | Haig | |
| 4,612,920 A | 9/1986 | Lower | |
| 4,621,628 A | 11/1986 | Brudermann | |
| 4,622,959 A | 11/1986 | Marcus | |
| 4,645,394 A * | 2/1987 | While et al. | 411/110 |
| 4,657,001 A * | 4/1987 | Fixel | 606/66 |
| 4,697,585 A | 10/1987 | Williams | |
| 4,705,027 A | 11/1987 | Klaue | |
| 4,754,749 A | 7/1988 | Tsou | |
| 4,776,330 A | 10/1988 | Chapman et al. | |
| 4,791,918 A | 12/1988 | Von Hasselbach | |
| 4,817,591 A | 4/1989 | Klaue | |
| 4,973,332 A | 11/1990 | Kummer | |
| 5,032,125 A | 7/1991 | Durham et al. | |
| 5,041,114 A | 8/1991 | Chapman et al. | |
| 5,041,115 A | 8/1991 | Frigg et al. | |
| 5,120,171 A | 6/1992 | Lasner | |
| 5,167,663 A | 12/1992 | Brumfield | |
| 5,176,681 A | 1/1993 | Lawes et al. | |
| 5,300,074 A | 4/1994 | Frigg | |
| 5,312,406 A | 5/1994 | Brumfield | |
| 5,364,398 A | 11/1994 | Chapman et al. | |
| 5,387,214 A * | 2/1995 | Kropf et al. | 606/64 |
| 5,454,813 A * | 10/1995 | Lawes | 606/62 |
| 5,484,439 A | 1/1996 | Olson et al. | |
| 5,549,610 A | 8/1996 | Russell et al. | |
| 5,573,536 A | 11/1996 | Grosse et al. | |
| 5,578,035 A | 11/1996 | Lin | |
| 5,591,168 A | 1/1997 | Judet et al. | |
| 5,658,287 A | 8/1997 | Hofmann et al. | |
| 5,658,339 A | 8/1997 | Tronzo et al. | |
| 5,713,901 A | 2/1998 | Tock | |
| 5,713,902 A | 2/1998 | Friedl | |
| 5,728,099 A | 3/1998 | Tellman et al. | |
| 5,741,256 A | 4/1998 | Bresina | |
| 5,772,662 A | 6/1998 | Chapman et al. | |
| 5,908,422 A | 6/1999 | Bresina | |
| 5,928,235 A | 7/1999 | Friedl | |
| 5,935,127 A | 8/1999 | Border | |
| 5,976,139 A | 11/1999 | Bramlet | |
| 6,010,506 A | 1/2000 | Gosney et al. | |
| 6,048,151 A | 4/2000 | Kwee | |
| 6,059,785 A | 5/2000 | Schavan et al. | |
| 6,123,708 A | 9/2000 | Kilpela et al. | |
| 6,126,661 A | 10/2000 | Faccioli et al. | |
| 6,187,007 B1 | 2/2001 | Frigg et al. | |
| 6,296,645 B1 | 10/2001 | Hover et al. | |
| 6,423,066 B1 * | 7/2002 | Harder et al. | 606/65 |
| 6,439,817 B1 * | 8/2002 | Reed | 411/110 |
| 6,443,954 B1 | 9/2002 | Bramlet et al. | |
| 6,454,810 B1 | 9/2002 | Lob | |
| 6,887,271 B2 * | 5/2005 | Justin et al. | 623/13.14 |
| 7,182,765 B2 | 2/2007 | Roth et al. | |
| 2002/0151898 A1 | 10/2002 | Sohngen et al. | |
| 2002/0173792 A1 | 11/2002 | Severns et al. | |
| 2003/0069581 A1 | 4/2003 | Stinson et al. | |
| 2003/0114855 A1 | 6/2003 | Wahl et al. | |
| 2006/0111716 A1 | 5/2006 | Schlienger et al. | |
| 2006/0149248 A1 | 7/2006 | Schlienger et al. | |
| 2006/0161155 A1 | 7/2006 | Schlienger et al. | |
| 2006/0189988 A1 | 8/2006 | Schlienger et al. | |
| 2006/0235395 A1 | 10/2006 | Frigg et al. | |
| 2006/0241605 A1 | 10/2006 | Schlienger et al. | |

FOREIGN PATENT DOCUMENTS

| | | | |
|---|---|---|---|
| DE | 196 29 011 A1 | 1/1998 | |
| DE | 199 45 611 A1 | 9/2001 | |
| EP | 0 251 583 A2 | 1/1988 | |
| EP | 0 321 170 B1 | 6/1989 | |
| EP | 0 381 462 A2 | 8/1990 | |
| EP | 0 411 273 | 2/1991 | |
| EP | 0 471 418 A1 | 2/1992 | |
| EP | 0 838 199 A1 | 4/1998 | |
| EP | 0 845 245 A2 | 6/1998 | |
| EP | 0 853 923 A1 | 7/1998 | |
| EP | 0 919 200 A1 | 6/1999 | |
| EP | 0 968 685 A2 | 6/1999 | |
| EP | 1016382 A2 * | 7/2000 | A61B 17/74 |
| EP | 1 053 718 A1 | 11/2000 | |
| EP | 1 214 914 A2 | 6/2002 | |
| EP | 1 260 188 A1 | 11/2002 | |
| EP | 1281365 | 2/2003 | |
| FR | 2 784 283 | 4/2000 | |
| GB | 2209947 A | 6/1989 | |
| JP | 09-066059 | 3/1997 | |
| JP | 09-066060 | 3/1997 | |
| JP | 09-066061 | 3/1997 | |
| JP | 11-137566 | 5/1999 | |
| JP | 2000-051224 | 2/2000 | |
| JP | 2000-051225 | 2/2000 | |
| JP | 2000-342596 | 12/2000 | |
| WO | WO 93/15679 | 8/1993 | |
| WO | WO 96/15737 | 5/1996 | |
| WO | WO 97/37606 | 10/1997 | |
| WO | WO 98/05263 | 2/1998 | |
| WO | WO 98/30164 | 7/1998 | |
| WO | WO 98/41161 | 9/1998 | |
| WO | WO 98/46169 | 10/1998 | |
| WO | WO 00/67653 | 11/2000 | |
| WO | WO 02/060331 | 8/2002 | |
| WO | WO 03/015649 | 2/2003 | |

OTHER PUBLICATIONS

International Search Report for International Application No. PCT/CH03/00157, mailed Oct. 20, 2003, English language translation of the German language version.

International Preliminary Examination Report for International Application No. PCT/CH03/00157, completed Sep. 1, 2004, German language version.

International Preliminary Examination Report for International Application No. PCT/CH03/00157, completed Sep. 1, 2004, English language translation of the German language version.

* cited by examiner

LOCKING SCREW FOR AN INTRAMEDULLARY NAIL

RELATED APPLICATION DATA

The present application is a continuation of the U.S. National Stage designation of co-pending International Patent Application No. PCT/CH2003/000157, filed Mar. 7, 2003, the entire content of which is expressly incorporated herein by reference thereto.

FIELD OF THE INVENTION

The present invention relates to orthopaedic implants and, more particularly, to a locking screw for use with an intramedullary nail, wherein the screw includes a head portion with a passage for receiving a longitudinal wedge element.

BACKGROUND OF THE INVENTION

The locking of intramedullary nails is known in the art, e.g., locking screws are introduced into the transverse boreholes of the intramedullary nail either with the help of an imaging method (X-ray control) or a fairly complicated targeting device. In both cases, a certain targeting inaccuracy is unavoidable, that is, the tip of the screw cannot be aligned exactly coaxially with the middle axis of the transverse borehole and, instead, deviates therefrom by a certain amount. So that the locking screw ends up in and can be passed through the transverse borehole in spite of this targeting error, the external diameter of the screw is underdimensioned relative to the diameter of the transverse borehole. If the targeting accuracy remains in the range of this underdimensioning, the locking screw can be passed through the transverse boreholes without problems in spite of the targeting error. However, because of the underdimensioning, there is a certain clearance between the locking screw and the transverse borehole.

This clearance defines the amount by which the main fragments of the bone, which are fixed in the corresponding locking hole by means of locking screws, can move relative to the nail and, accordingly, because of the rigidity of the nail, also relative to other main bone fragments fastened with the same nail. Together with the flexibility of the material and of the overall device, this may cumulatively assume a magnitude, which prevents successful healing or delays it significantly. Admittedly, this clearance is unavoidable in order to guarantee the applicability of the locking for the surgeon. However, it is clinically undesirable for certain indications, such as metaphysical fragments.

Even nails with a full cross section, which may have an internal thread in the locking hole, are not without clearance. The internal thread merely prevents the nail from moving axially on the locking screw.

SUMMARY OF THE INVENTION

The present invention has been developed to solve this problem. It is an object of the invention to create a locking screw, with which the gap or clearance, existing between it and the intramedullary nail, can be eliminated and the locking screw can be wedged in the transverse borehole of the intramedullary nail.

Pursuant to the invention, this objective is accomplished with a locking screw having a central longitudinal axis, a screw shaft, at least a portion of which includes an external thread having an outer diameter, and a screw head having a diameter greater than the outer diameter of the external thread. A passage is formed through the screw head configured and dimensioned to receive a longitudinal wedging element, the passage extending in a first direction generally parallel to the longitudinal axis of the screw.

The advantages, achieved by the invention, are seen to lie essentially therein that, due to the inventive locking screw, the clearance between the intramedullary nail and the locking screw can be eliminated. However, the invention also permits the screw to be introduced in a first phase with clearance and to eliminate this clearance only subsequently. A further advantage consists therein that, in spite of the elimination of the clearance, the ability to rotate the locking screw is not blocked. The advantages of retaining the ability to rotate are manifold:

the locking screw can be screwed in and out even in the state of reduced clearance (axial freedom) and in the case of a failure of the locking screw, it is possible to extract the locking screw with conventional techniques (by beating or pulling it out).

In the case of a special embodiment of the invention, the shaft of the screw has a first groove, which extends in the direction of the passage and preferably has a partially circular or polygonal cross-section. This construction saves space, requires a lower pressing-in force and guarantees good guidance of the wedging element.

In a further embodiment, the shaft of the screw has a second groove, which is disposed essentially parallel to the first groove, offset radially by the rotation angle alpha and is deeper than the first groove. The passage in the head of the screw is constructed as an elongated hole, into which both grooves terminate. Between the two grooves, there is a ramp, which arises from the first groove to the second groove. The angle of rotation alpha may assume a value of 40° to 120° and preferably of 60° to 90°.

This embodiment has the advantage that the wedging takes place more quickly and can also be undone again more quickly. The wedging force is also increased significantly with the application of a (comparatively) lower force. Since the wedging force is applied over a torque, the user has to apply only a relatively slight force.

In the case of a further embodiment, the groove tapers in cross section with increasing distance from the head of the screw. By these means, on the one hand, the wedging or reduction in clearance is accomplished more quickly and, on the other, the wedging can be undone again more quickly.

For a further embodiment, the groove makes an angle with the longitudinal axis of the locking screw, which preferably is less than 5°.

The groove may have a depth, which is between 1% and 50% and preferably between 2% and 20% of the diameter of the shaft of the screw.

Advisably, the inventive locking screw is introduced into the transverse borehole of an intramedullary nail, for which the diameter of the transverse borehole is larger than the external diameter of its external thread. When a longitudinal wedging element is introduced into the passage of the locking screw, wedging takes place between the shaft of the locking screw and the inner surface of the transverse borehole of the medullary nail.

The longitudinal wedging element may be a wire, preferably with an end, the cross-section of which is tapered. Advisably, the passage of the locking screw has a borehole, which corresponds to the cross-section of the wire.

Alternatively, the longitudinal wedging element may have a cross-sectional profile, which corresponds to the cross-sectional profile of the passage and preferably is constructed wedge-shaped. The passage may be essentially circular with a diameter of 0.5-2.0 mm and preferably of 0.8-1.2 mm. The longitudinal wedging element typically has a length, which corresponds to at least two thirds of the shaft of the screw. At one of its ends, the longitudinal wedging element may have a stop for the head of the screw. With that, the wedging element is prevented from piercing through the passage.

The passage may also be provided with an internal thread. The longitudinal wedging element may also have an external thread, which corresponds to the internal thread of the passage.

BRIEF DESCRIPTION OF THE DRAWINGS

The invention and further developments of the invention are explained in even greater detail in the following by means of the partially diagrammatic representations and drawings of several examples, in which.

DETAILED DESCRIPTION OF THE PREFERRED EMBODIMENTS

Figure 1:
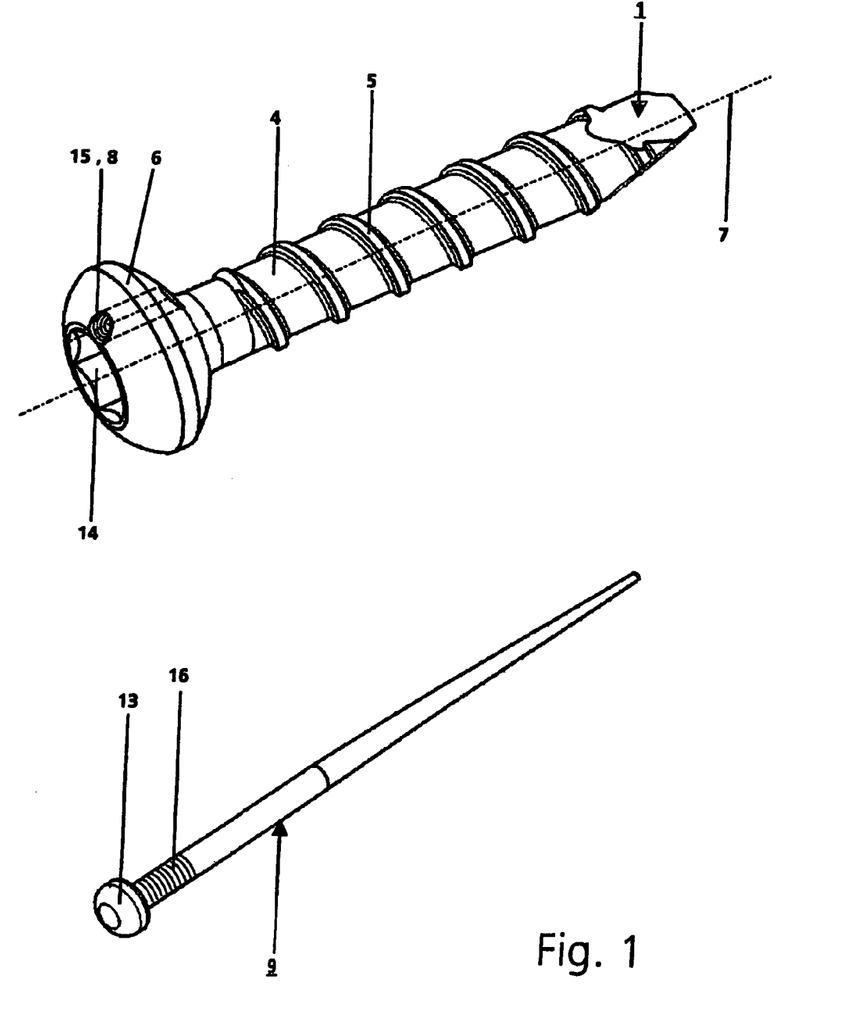
FIG. 1 shows a perspective view of a locking screw with a passage in the head of the screw and a locking element.
Figure 2:
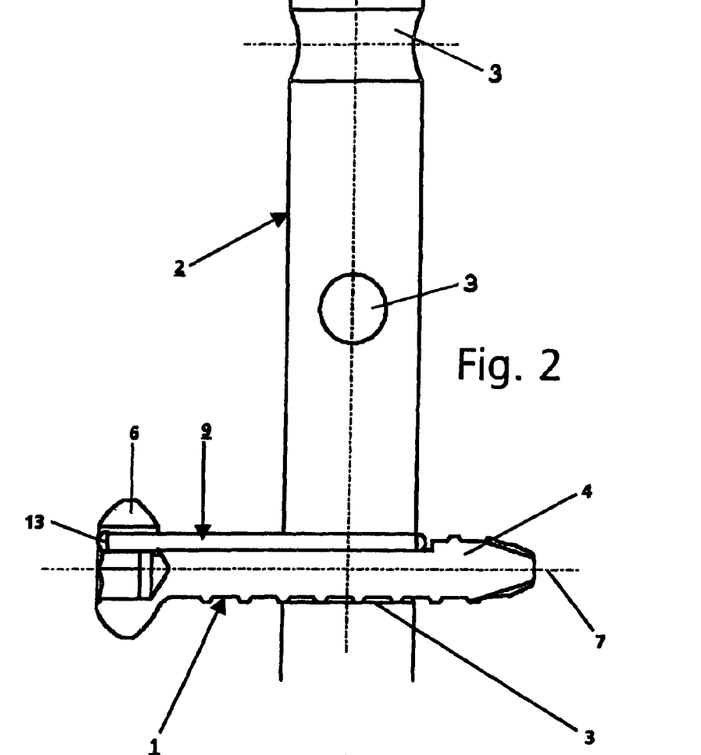
FIG. 2 shows a longitudinal section through an intramedullary nail, in the transverse borehole of which the locking screw of FIG. 1 is inserted.

The locking screw 1, shown in FIG. 1, is used for locking an intramedullary nail 2, which is shown in FIG. 2 and has several transverse boreholes 3. The locking screw 1 has a central longitudinal axis 7 and comprises a screw shaft 4, which is provided with an external thread 5, as well as a screw head 6, with a hexagonal socket 14, in order to be able to turn the locking screw 1 in one of the transverse boreholes 3 of the intramedullary nail 2.

The diameter of the screw head 6 is larger than the external diameter of the external thread 5, the screw head 6 having a passage 8 in the form of a circular borehole, which extends essentially parallel to the longitudinal axis 7 and to the external thread 5 and has an internal thread 15 for accommodating a longitudinal wedging element 9 in the form of a conically extending nail with a partial external thread 16 and a stop 13 at the head, the external thread 16 corresponding to the internal thread 15. The wedging element 9 has a length, which corresponds approximately to two thirds of the length of the screw shaft 4.

Figure 3:
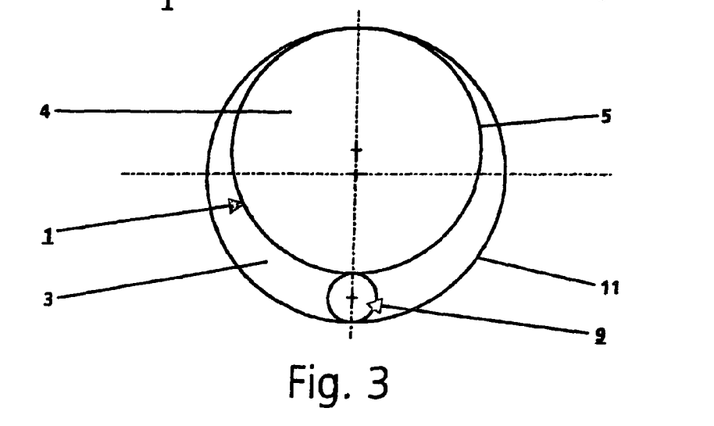
FIG. 3 shows a longitudinal section through the intramedullary nail of FIG. 2, offset by 90°, in the region of its transverse borehole.
Figures 4, 5:
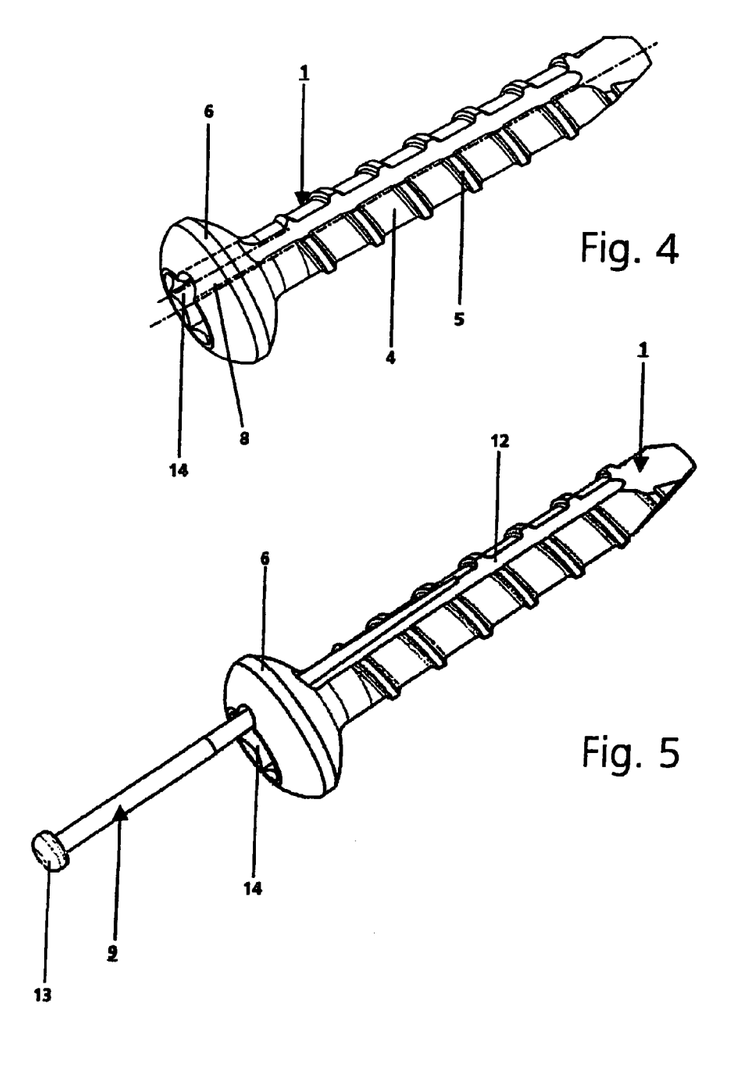
FIG. 4 shows a perspective view of a modified locking screw with a borehole in the head of the screw and a longitudinal groove in the shaft of the screw.
FIG. 5 shows a perspective view of the locking screw of FIG. 4 with a longitudinal wedging element introduced into the head of the screw.

In FIG. 3 it is shown how the wedging element 9 can be wedged between the inner surface 11 of the transverse borehole 3 and the external diameter of the external thread 5 of the locking screw 1. It is a prerequisite for this that the external diameter of the external thread 5 is smaller than the diameter of the transverse borehole 3.

Figure 6:
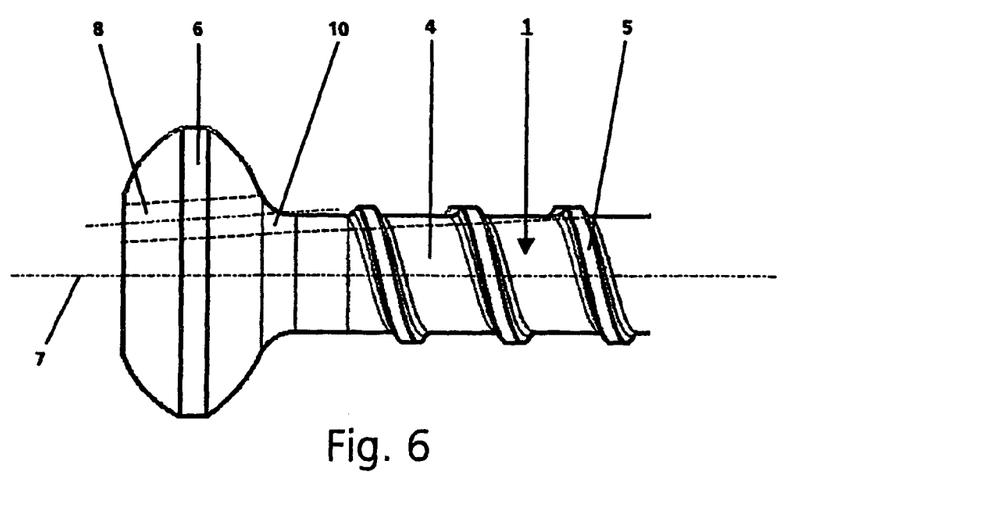
FIG. 6 shows an enlarged longitudinal section through the modified locking screw of FIG. 4.
Figure 7:
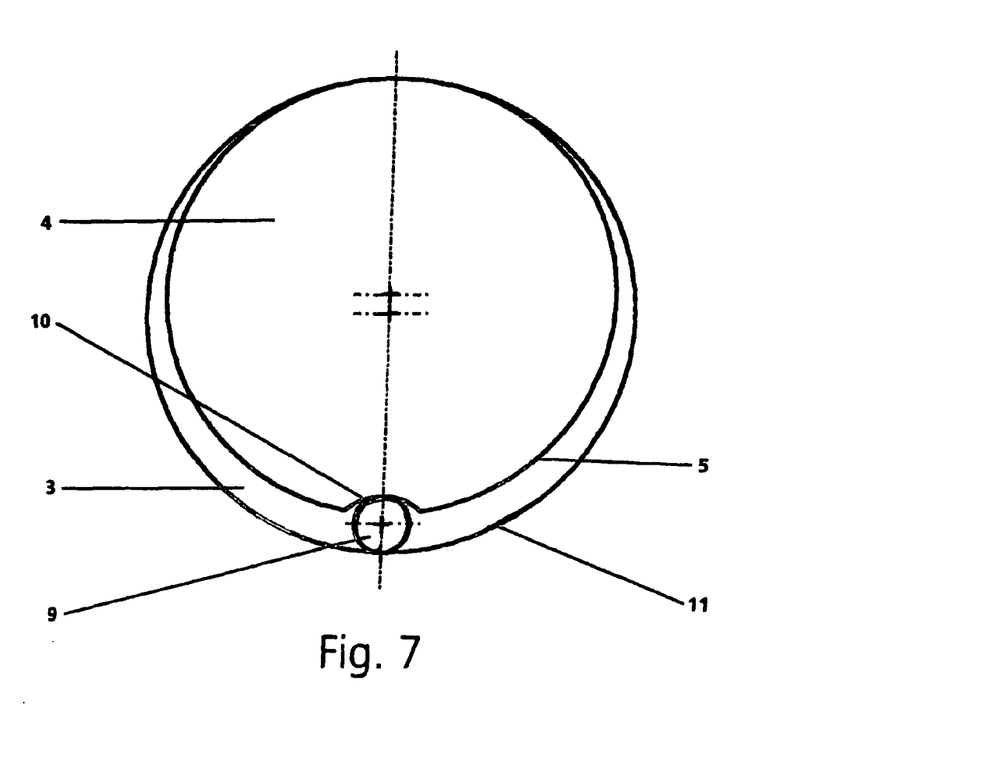
FIG. 7 shows a cross section through a modified locking screw of FIG. 4 in the region of the transverse borehole of the intramedullary nail.

As shown in FIGS. 2 and 6, the longitudinal wedging element 9, at its rear end, has a stop 13, so that it cannot be forced further into the screw head 6. By these means, it is prevented that the wedging element 9 can reach the intramedullary nail.

In FIGS. 4-7, a variation of the locking screw 1 is shown, for which the screw shaft 4 has a groove 10 with a partially circular cross-section, flush with the passage 8 (in the form of a circular borehole with a diameter typically of 1 mm). The groove 10 tapers conically as the distance from the screw head 6 increases. The groove 10 has a depth of 5% of the diameter of the screw shaft 4. For this variation, the wedging element 9, which also tapers conically, is wedged between the inner surface 11 of the transverse borehole 3 and the inner surface of the groove 10.

Figure 8:
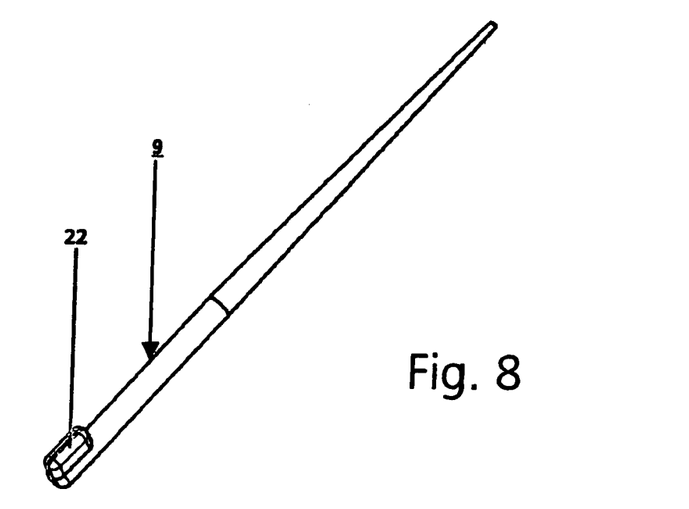
FIG. 8 shows a perspective view of a modified locking screw with a keyhole shaped passage and a keyhole shaped locking element.

In FIG. 8, a further variant of the locking screw 1 is shown, for which the passage 8 is realized in the form of a keyhole-shaped groove for accommodating a longitudinal wedging element 9 in the form of a rod, which has a keyhole-shaped profile 22 at its head end and corresponds to the keyhole-shaped groove. The wedging element 9 is secured against twisting relative to the passage 8 by the shape of the keyhole-shaped profile 22.

In FIGS. 9 to 12, a further embodiment of the locking screw 1 is shown. For this variation, the screw shaft 4, aside from a first groove 10, has a second groove 16, which extends parallel to the first groove 10, is offset radially by the rotation angle alpha of 50° and is deeper than the first groove 10. Moreover, the first groove 10 is connected with the second groove 16 over a wedge-shaped ramp 18. The passage 8 in the screw head 6 is constructed as an elongated hole, which corresponds to the geometry of the ramp 18 and in which the two grooves 10, 16 terminate, so that the longitudinal locking element 9 can be placed in the first groove 10 as well as in the second groove 16.

Figure 9:
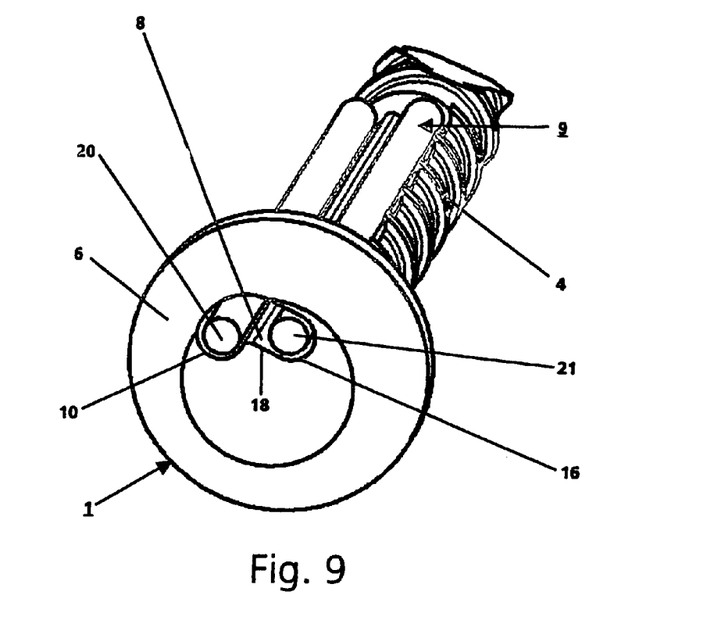
FIG. 9 shows a perspective view of a modified locking screw with two grooves.
Figure 10:
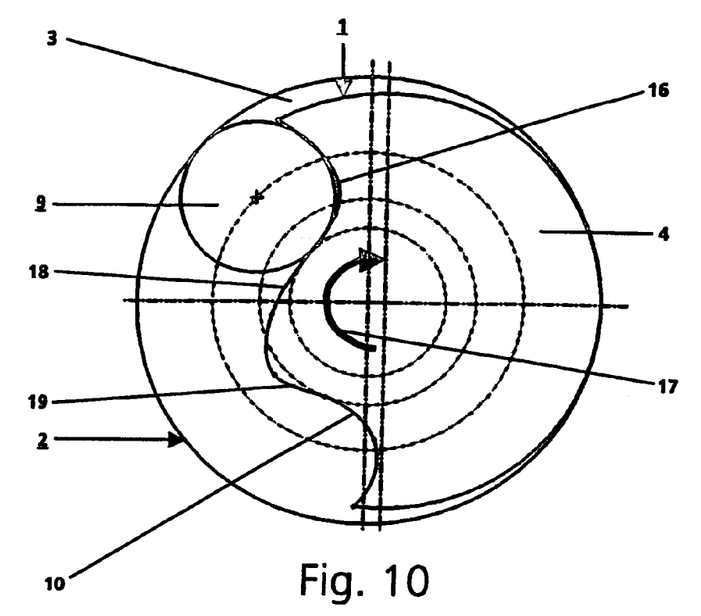
FIG. 10 shows a cross section through the locking screw of FIG. 9 of a first, unwedged position.
Figure 11:
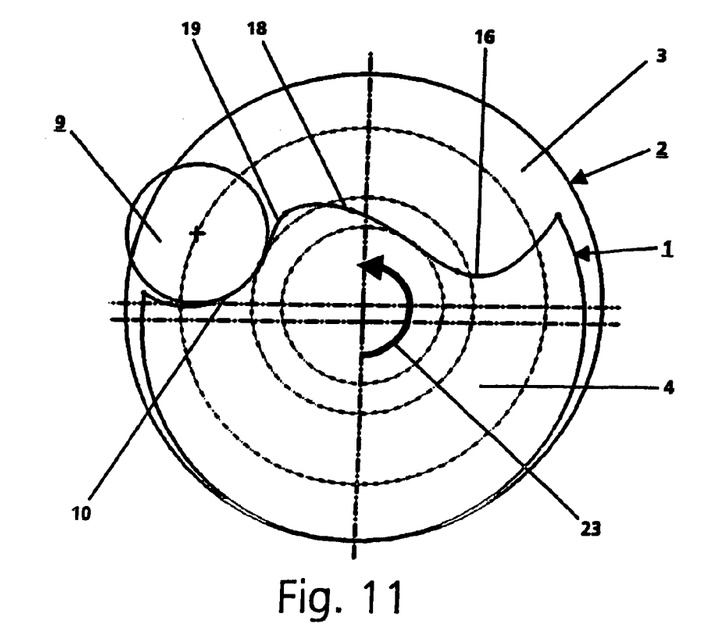
FIG. 11 shows a cross section through a locking screw of FIG. 9 with a second, wedged position.

By rotating the locking screw 1 in the direction of arrow 17 (clockwise), the longitudinal locking element 9 (un-wedged position in FIG. 10), lying in the second groove 16, slides along the relatively flat, wedge-shaped ramp 18 until it falls into the first groove 10 of lesser depth (wedged position in FIG. 11). The longitudinal locking element 9 is prevented from sliding from the first groove 10 back into the second groove 16 by the relatively steep flank 19 and the camber relative to the positions 20 and 21 between the two grooves 10, 16. At the same time, the longitudinal locking element 9 moves in the elongated hole 8 from position 21 to position 20 (FIG. 9).

By rotating the locking screw 1 in the direction of arrow 23 (counterclockwise), the longitudinal locking element 9 (wedged position in FIG. 11), lying in the first groove 10, falls back into the second groove 16 (not wedged position in FIG. 10), so that the clamping of the locking screw 1 is canceled once again.

Figure 12:
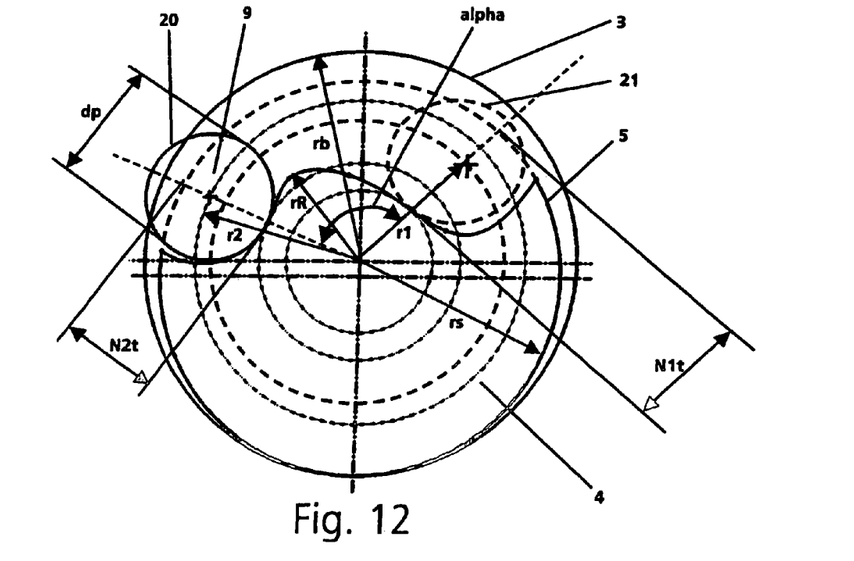
FIG. 12 shows a diagrammatic cross-sectional representation of the locking screw of FIG. 9 with a first and second position of the locking screw.

As shown in FIG. 12, the dimensioning of the individual components advantageously should be as follows:

the distance between the midpoint of the longitudinal locking element 9 and the midpoint of the screw shaft 4 in position 21 (broken lines) is $r_1$;

the distance between the midpoint of the longitudinal locking element 9 and the midpoint of the screw shaft 4 in position 20 (continuous lines) is $r_2$, $r_2$ being greater than $r_1$;

the diameter of the longitudinal locking element 9 is dp, the radius of the external thread 5 of the screw shaft 4 is $r_1$ the diameter of the transverse borehole 3 is $r_b$, $r_b > r_s$, the desired press fit or the reduction in clearance between the external thread 5 of the screw shaft 4, the longitudinal locking element 9 and the transverse borehole 3 of the intramedullary nail arises if the sum of $[(r_s - N_{2t} + d_p) + r_s)]$ is greater than or equal to $2r_b$, $N_{2t}$ being the depth of the groove in position 20.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A locking screw for an intramedullary nail having at least one transverse borehole, the locking screw having a central longitudinal axis and comprising:
a screw shaft, at least a portion of which includes an external thread having an outer diameter;
a screw head having a diameter greater than the outer diameter of the external thread; and
a passage formed through the screw head configured and dimensioned to receive a longitudinal wedging element to be passed therethrough into a clearance between an outer surface of the external thread and an inner surface of the transverse borehole, the passage extending in a first direction generally parallel to the longitudinal axis of the screw, wherein the longitudinal wedging element is introduced through the passage in the screw head and is configured and dimensioned to be wedged between the screw shaft of the locking screw and an inner surface of the transverse borehole in the intramedullary nail, and wherein the longitudinal wedging element has a tapering a cross-sectional profile corresponding to the cross-sectional profile of the passage.

2. The locking screw of claim 1, wherein the screw shaft includes a first groove extending in the first direction of the passage.

3. The locking screw of claim 2, wherein the first groove has a partially circular or polygonal cross-section.

4. The locking screw of claim 2, wherein the screw shaft includes a second groove which is deeper than the first groove, the second groove disposed generally parallel to the first groove and offset radially by a rotation angle.

5. The locking screw of claim 4, wherein the passage in the screw head is configured as an elongated hole, and both the first and second grooves terminate at the passage.

6. The locking screw of claim 4, wherein the rotation angle between the first and second grooves is between 40° and 120°.

7. The locking screw of claim 4, wherein the rotation angle between the first and second grooves is between 60° and 90°.

8. The locking screw of claim 4, further comprising a ramp surface formed between the first and second grooves and rising from the first groove to the second groove.

9. The locking screw of claim 4, wherein characterized in that the depth of the second groove is such that the longitudinal wedging element can be introduced into the second groove with clearance relative to the transverse borehole.

10. The locking screw of claim 2, wherein the first groove tapers in cross-section as its distance from the screw head increases.

11. The locking screw of claim 2, wherein the first groove forms an angle with the longitudinal axis of the screw.

12. The locking screw of claim 11, wherein the angle between the first groove and the longitudinal axis of the screw is less than 5°.

13. The locking screw of claim 2, wherein the screw shaft has a diameter and the first groove has a depth, and the depth of the first groove is between 1% and 50% of the diameter of the screw shaft.

14. The locking screw of claim 13, wherein the depth of the first groove is between 2% and 20% of the diameter of the screw shaft.

15. The locking screw of claim 1, wherein the longitudinal wedging element includes a stop surface at one of its ends for engaging the screw head.

16. The locking screw of claim 1, wherein the passage has a generally circular cross-section with a diameter of between 0.5 mm and 2.0 mm.

17. The locking screw of claim 16, wherein the diameter of the passage is between 0.8 mm and 1.2 mm.

18. A locking screw for an intramedullary nail having at least one transverse borehole, the locking screw having a central longitudinal axis and comprising:
a screw shaft, at least a portion of which includes an external thread having an outer diameter;
a screw head having a diameter greater than the outer diameter of the external thread; and
a passage formed through the screw head configured and dimensioned to receive a longitudinal wedging element to be passed therethrough into a clearance between an outer surface of the external thread and an inner surface of the transverse borehole, the passage extending in a first direction generally parallel to the longitudinal axis of the screw, wherein the longitudinal wedging element is introduced through the passage in the screw head and is configured and dimensioned to be wedged between the screw shaft of the locking screw and an inner surface of the transverse borehole in the intramedullary nail, wherein the screw shaft has a first length, the longitudinal wedging element has a second length, and the second length is at least two thirds (⅔) as long as the first length.

19. A locking screw for an intramedullary nail having at least one transverse borehole, the locking screw having a central longitudinal axis and comprising:
a screw shaft, at least a portion of which includes an external thread having an outer diameter;
a screw head having a diameter greater than the outer diameter of the external thread; and
a passage formed through the screw head configured and dimensioned to receive a longitudinal wedging element to be passed therethrough into a clearance extending between an an outermost surface of the external thread and an inner surface of the transverse borehole, the passage extending in a first direction generally parallel to the longitudinal axis of the screw, wherein the passage includes an internal thread and wherein the outermost surface of the external thread is defined by the greatest radial dimension of the external thread.

20. The locking screw of claim 19, wherein the longitudinal wedging element has an external thread, which corresponds to the internal thread of the passage.

* * * * *